US007759058B2

(12) United States Patent
Bretler

(10) Patent No.: US 7,759,058 B2
(45) Date of Patent: Jul. 20, 2010

(54) ANTI-MICROBIAL PERFUMING COMPOSITIONS

(75) Inventor: Gil Bretler, Geneva (CH)

(73) Assignee: Firmenich SA, Geneva (CH)

(*) Notice: Subject to any disclaimer, the term of this patent is extended or adjusted under 35 U.S.C. 154(b) by 701 days.

(21) Appl. No.: 10/962,075

(22) Filed: Oct. 7, 2004

(65) Prior Publication Data

US 2005/0049301 A1    Mar. 3, 2005

Related U.S. Application Data

(63) Continuation-in-part of application No. 10/106,649, filed on Mar. 25, 2002, now abandoned, which is a continuation of application No. PCT/IB00/01389, filed on Sep. 28, 2000.

(30) Foreign Application Priority Data

Oct. 4, 1999    (WO) .................... PCT/IB99/01618
Oct. 11, 1999   (WO) .................... PCT/IB99/01660

(51) Int. Cl.
*C12P 13/04*    (2006.01)
(52) U.S. Cl. .......................................... 435/6
(58) Field of Classification Search ............... 435/6
See application file for complete search history.

(56) References Cited

U.S. PATENT DOCUMENTS

| 4,488,973 | A |   | 12/1984 | Hill et al. ................ 424/69 |
| 4,675,327 | A | * | 6/1987  | Fredrick ................. 514/383 |
| 5,180,749 | A | * | 1/1993  | Cusack et al. ........... 514/726 |
| 5,403,587 | A |   | 4/1995  | McCue et al. ........... 424/195 |
| 5,420,104 | A |   | 5/1995  | Holzner et al. ............ 512/2 |
| 6,106,854 | A | * | 8/2000  | Belfer et al. ............. 424/405 |
| 6,403,109 | B1 | * | 6/2002 | Stora ..................... 424/401 |
| 6,613,728 | B1 | * | 9/2003 | Sirianni et al. .......... 510/382 |

FOREIGN PATENT DOCUMENTS

EP    0 451 889 A1    10/1991
WO    WO 98/02044    1/1998

OTHER PUBLICATIONS

Dabbah et al.; "Antimicrobial Action of Some Citrus Fruit Oils on Selected Food-Borne Bacteria," Applied Microbiology, Jan. 1970, vol. 19, No. 1, p. 27-31. (5 pages total).*
Holzner, XP-000929204,"The examination of the effectiveness of body deodorant sprays" Aerosol Report, vol. 25, pp. 354-369, (1986.
Morris et al., XP 000645444, "Antimicrobial Activity of Aroma Chemicals and Essential Oils", Journal of the American Oil Chemists' Society Champaign, US, pp. 595-603 (1979).

* cited by examiner

*Primary Examiner*—Susan B McCormick Ewoldt
(74) *Attorney, Agent, or Firm*—Winston & Strawn LLP

(57) ABSTRACT

The present invention describes perfumes and perfuming compositions having an anti-microbial activity and containing effective amounts of certain perfuming ingredients which have an anti-microbial activity as evaluated by the Microbial Reduction Test.

9 Claims, No Drawings

ANTI-MICROBIAL PERFUMING COMPOSITIONS

CROSS-REFERENCE TO RELATED APPLICATIONS

This application is a continuation-in-part of application Ser. No. 10/106,649, filed Mar. 25, 2002 now abandoned, which in turn is a continuation of International application PCT/IB00/01389 filed Sep. 28, 2000. The entire content of these applications is expressly incorporated herein by reference thereto.

TECHNICAL FIELD AND PRIOR ART

The present invention concerns the field of perfuming ingredients and compositions which have an anti-microbial effect. The application also describes a new test which is particularly adapted for determining the anti-microbial activity of perfuming ingredients.

In the perfume industry as well as in industries in which perfumes and perfuming compositions are used (as, for example, in companies which manufacture dish-washing liquids, all-purpose cleaners, shampoos or even cosmetic products), there is a great tendency towards the creation and use of perfuming compositions having an anti-microbial effect. This is due to the fact that there is an increasing consumer demand for products which have both an activity against bacteria and other microorganisms, and fulfill the consumer's expectations with regard to their lack of content in the currently used biocides such as Triclocarban and Triclosan.

It is known that certain perfuming ingredients of synthetic and natural origin do not only have a pleasant odor, but also have a more or less pronounced activity against microorganisms. However, this potential use of the perfuming ingredients has not been exploited in the past. The reason for this arises, to a great part, from the fact that there does not exist, according to our knowledge, a test allowing the evaluation in a quantitative, safe and reproducible way, of the true anti-microbial properties of perfuming ingredients.

European patent application 451 889 to Unilever provides a general survey of the various tests which are known to determine a certain anti-microbial activity of known perfuming compounds. The conclusion in the above application is that the methods disclosed are not reliable, e.g. because conflicting results have been obtained for a given ingredient against one and the same microorganism, or because results obtained for a certain microorganism cannot be transferred to another microorganism. As a solution to this problem, this prior art document describes a test called individual challenge test which is said to give reliable data on a compound's anti-microbial activity.

However, this known test does not provide quantitative results which permit a real evaluation of a compound's activity. Furthermore, the surfactants employed in the concentrations indicated (iso-octyl-phenoxypolyethoxy-ethanol and sodium dodecyl sulfate) do not solubilize the hydrophobic perfuming ingredients in the aqueous solution. The perfuming ingredient will be present to a greater part as a suspension of micelles. Therefore, they will not make proper contact with the inoculated bacteria, which are present in the aqueous phase. This creates an inherent error in the measurement and renders the procedure unreliable.

SUMMARY OF THE INVENTION

The invention relates to a method for evaluating the anti-microbial activity of a perfuming ingredient. This method includes the steps of solubilizing the ingredient to be tested in an aqueous medium at a concentration between 250 and 1000 µg/ml, relative to the medium, in the presence of an effective amount of solvent which is substantially non-toxic for a subsequently added bacteria and which allows a complete solubilizing of the perfuming ingredient; adding an inoculum of a desired bacteria such that the final concentration in the medium is at least $10^7$ colony forming units/ml of the medium; diluting the medium so as to reduce the bacteria concentration to $10^3$ colony forming units/ml of medium; spreading $10^2$ colony forming units/ml of the bacteria onto an appropriate culture medium; counting the surviving colonies after incubation; and comparing the value obtained with a control that contains no perfume.

The solvent is an alcohol, preferably ethanol, and is present at a concentration in the aqueous medium of between 5 and 20% by weight with respect to the total weight of the medium. The bacteria, preferably one selected from the group consisting of *Escherichia coli, Pseudomonas aeruginosa, Staphylococcus aureus* and *Enterococcus hirae*, contacts the culture medium for a time of about 5 min. Also, the perfuming ingredient is generally present in the aqueous medium at a concentration of between 400 and 600 µg/ml.

The present invention also relates to an anti-microbial composition containing at least 30% by weight of one or more active perfuming ingredients. The anti-microbial activity of the composition is 100% against at least 2 different kinds of bacteria selected from the group consisting of *Escherichia coli, Pseudomonas aeruginosa, Staphylococcus aureus* and *Enterococcus hirae*. This activity is measurable by the previously described method. The active perfuming ingredient is preferably chosen from the group consisting of decanal, 10-undecen-1-al, nonanal, 4-isopropylbenzaldehyde, 4-undecanolide, citronellal, citronellal, cyclamen aldehyde, delphone, dihydroeugenol, 8-p-menthanol, dimetol, geraniol, 3-(1,3-benzodioxal-5-yl)-2-methylpropanal, isoeugenal, nerol, tetrahydrolinalool, zestover, intreleven aldehyde, (2E, 6Z)-2,6-nonadien-1-ol, γ-dodecalactone, floralozone, isobutylquinoleine, LILIAL®, MAYOL®, phenylhexanol, and 9-decen-1-ol.

In a preferred embodiment, the active perfuming ingredient that is not a straight chain saturated aldehyde. This active perfuming ingredient is preferably chosen from the group consisting of 10-undecen-1-al, 4-isopropyl benzaldehyde, 4-undecanolide, citronellal, citronellol, cyclamen aldehyde, delphone, dihydroeugenol, 8-p-menthanol, dimetol, geraniol, 3-(1,3-benzodioxal-5-yl)-2-methylpropanal, isoeugenal, nerol, tetrahydrolinalool, zestover, intreleven aldehyde, (2E,6Z)-2,6-nonadien-1-ol, γ-dodecalactone, floralozone, isobutylquinoleine, LILIAL®, MAYOL®, phenylhexanol, 9-decen-1-ol or mixtures thereof.

The compositions which contain at least 50% by weight of active perfuming ingredients are the more preferred ones.

Another embodiment of the invention is a perfuming composition or perfumed article containing an anti-microbial perfuming composition disclosed herein. The perfumed article is preferably in the form of a soap, a bath or shower gel, a shampoo or other hair-care product, a deodorant or antiperspirant, a cosmetic preparation, an air-freshener, a liquid or solid detergent for the treatment of textiles, a fabric softener or an all-purpose cleaner for household or industrial use.

Yet another embodiment is a method for imparting an anti-microbial activity or enhancing the anti-microbial activity of an article for personal care or a functional product which comprises adding an anti-microbial composition according to the invention to a personal care or a functional product.

DETAILED DESCRIPTION OF THE PREFERRED EMBODIMENTS

We have now developed a test which allows a quantitative and reliable evaluation of the anti-microbial activity of perfuming ingredients against a variety of different bacteria strains. This test is called "Microbial Reduction Test", and the test is particularly appropriate for perfuming ingredients.

In this specific "Microbial Reduction Test," the perfuming ingredient to be evaluated is weighed into an aqueous test solution in a certain concentration as explained below and is solubilized with an appropriate solvent which does not negatively affect the bacteria in the inoculum that is to be added at a later stage. The appropriate solvents can be of a large variety of alcohols, for example, isopropanol, amyl alcohols and fusel oils. The preferred alcohol, however, is ethanol. We have surprisingly discovered that the addition of alcohols, and in particular of ethanol, makes it possible to obtain reliable and significant results on the anti-microbial activity of a perfuming ingredient, although it is known that ethanol itself has a certain bacteriostatic effect. However, we have surprisingly found that the use of the right amount of ethanol in the test according to the present invention has such a low effect on the bacteria that significant data of the anti-microbial activity of the test perfuming ingredient can be obtained. At the same time, the ethanol ensures a good solubilization of the hydrophobic perfuming ingredient in the aqueous phase which is used as a test medium.

The amount of ethanol to be used depends on the amount of perfuming ingredient present in the solution. The concentration of the latter will be between 250 and 1000 µg/ml, preferably between 300 and 800 µg/ml, with the most preferred concentration ranging between 400 and 600 µg/ml. For the latter, it was found that ethanol concentrations in the test solution of between 5 and 20% by weight gave good results, the preferred concentration being around 15% by weight, based on the total weight of the test solution. These values are given with respect to the final aqueous solution containing the perfume, the ethanol and the inoculum.

When the perfuming ingredient is then solubilized in the test solution, at the above-identified concentrations, the solution is inoculated with the respective test bacterium to provide a final concentration of bacteria of $10^7$ colony forming units (CFU)/ml.

The following bacteria were used:
*Escherichia coli*, ATCC 10536 (origin: American Type Culture Collection, Rockville, Md.)
*Pseudomonas aeruginosa*, CNCN A22 (origin: Institut Pasteur, Paris)
*Staphylococcus aureus*, ATCC 9144 (origin: Oxford Assay)
*Enterococcus hirae*, ATCC 10541 (origin: FDA, USA).

After a contact time of between 2 and 10 min, preferably about 5 min at about 20° C., the aqueous test solution is then diluted with saline water to a concentration of about $10^3$ CFU/ml. At this high dilution, the action of the perfuming ingredient on the bacteria is negligible. A volume corresponding to a theoretical maximum of $10^2$ CFU's is then removed, spread on a culture medium, incubated and the number of colonies is counted. In practice, the test will in general be carried out by adding 0.1 ml test sample (containing $10^7$ CFU's), to 9.9 ml of saline water and repeating the dilution with the solution obtained, until the desired concentration of about $10^3$ CFU/ml was reached. From this solution, a 0.1 ml sample was spread on a casein-peptone dextrose yeast agar plate. The bacteria were then grown under appropriate conditions. We found that good results were obtained when the bacteria were grown overnight in an incubator at 37° C. and a humidity of about 60-90%. The number of colonies were then evaluated, for example with a standard colony counter.

An anti-microbial activity rate for the respective product tested is then established by dividing the number of colony forming units for the bacteria exposed to the test product by the number of colony forming units counted in a reference or control test in which the same bacterium has been submitted to the same testing sequence as above but without addition of a perfuming ingredient.

A perfuming ingredient is said to have successfully passed the test, i.e. is said to have an anti-microbial activity, when 100% of the respective bacteria have been eliminated.

According to the invention, the active molecules are defined as compounds which are active against 100% of the bacteria of two or three of the strains mentioned above. A non-limiting list of the compounds obeying the conditions of the present invention is given hereinbelow:

| | |
|---|---|
| Decanal | Isoeugenal |
| 10-Undecen-1-al | Nerol |
| Nonanal | Tetrahydrolinalool |
| 4-Isopropylbenzaldehyde | Zestover[3] |
| 4-Undecanolide | Intreleven aldehyde[4] |
| Citronellal | (2E,6Z)-2,6-nonadien-1-ol |
| Citronellol | γ-Dodecalactone |
| Cyclamen aldehyde | Floralozone[5] |
| Delphone[1] | Isobutylquinoleine |
| Dihydro eugenol | Lilial ®[6] |
| 8-p-Menthanol | Mayol ®[7] |
| Dimetol[2] | Phenylhexanol |
| Geraniol | 9-Decen-1-ol |
| 3-(1,3-Benzodioxal-5-yl)-2-methylpropanal | |

[1] 2-Pentyl-1-cyclopentanone; origin: Firmenich SA, Geneva, Switzerland
[2] 2,6-Dimethyl-2-heptanol; origin: Givaudan-Roure SA, Vernier, Switzerland
[3] 2,4-Dimethyl-1-carbaldehyde; origin: Firmenich SA, Geneva, Switzerland
[4] origin: International Flavors & Fragrances, USA
[5] mixture of 3-(4-ethylphenyl)-2,2-dimethylpropanal + 3-(2-ethylphenyl)-2,2-dimethylpropanal; origin: International Flavors & Fragrances, USA
[6] origin: Givaudan-Roure SA, Vernier, Switzerland
[7] cis-7-p-menthanol; origin: Firmenich SA, Geneva, Switzerland In one embodiment, the primary active perfuming ingredient is not a straight chain saturated aldehyde. Of course, other perfuming ingredients or co-ingredients can be included so long as they do not detract from the antimicrobial activity of the primary active perfuming ingredient.

Therefore, in the context of the present invention, an active molecule is defined as a compound having an anti-microbial activity as tested by the Microbial Reduction Test when it falls under the list given here-above. The use of these compounds as anti-microbial agents is another object of the present invention.

The present invention discloses compositions having an anti-microbial action and containing an effective amount of active molecules as defined above. We have found that, in order to be effective, such compositions should contain at least about 30% by weight, of the above-defined active molecules, with respect to the total weight of the composition. The preferred compositions are those which contain about 50% by weight of active molecules, with respect to the total weight of the composition.

The invention also discloses perfuming compositions or perfumed products that include a consunable component and that contains one of the anti-microbial compositions defined herein.

It is hence possible to prepare perfumes and colognes having an anti-microbial activity, by using a composition comprising active molecules according to the present invention, thus providing anti-microbial perfuming compositions. The anti-microbial perfuming compositions as defined above can advantageously be used to perfume certain products, in particular consumer products in the field of household and body care.

As it will appear from the examples below, these products, thanks to the presence of the anti-microbial compositions incorporated therein, acquire an anti-microbial activity themselves.

The activity of the final products will of course depend on the amount of perfuming composition present. Non-limiting examples for this type of application include soaps, bath and shower gels, shampoos, deodorants and antiperspirants, cosmetic compositions, air-fresheners, liquid and solid detergents for the treatment of textiles, fabric softeners and all-purpose cleaners for household and also industrial use.

In these applications, the anti-microbial compositions can be used alone or in admixture with other perfuming ingredients, solvents or adjuvants of current use in perfumery. The nature and the variety of these coingredients do not require a more detailed description here, which, moreover, would not be exhaustive, and the person skilled in the art will be able to choose the latter through its general knowledge and as a function of the nature of the product to be perfumed and of the desired olfactive effect. These perfuming ingredients belong to chemical classes as varied as alcohols, aldehydes, ketones, esters, ethers, acetates, nitriles, terpene hydrocarbons, sulfur- and nitrogen-containing heterocyclic compounds, as well as essential oils of natural or synthetic origin. A large number of these ingredients is moreover listed in reference textbooks such as the book of S. Arctander, Perfume and Flavor Chemicals, 1969, Montclair, N.J., USA, or its more recent versions, or in other works of similar nature.

EXAMPLES

The invention will now be illustrated in greater detail in the following examples.

Example 1

An anti-microbial composition was prepared with the following ingredients:

| Ingredients | Parts by weight |
| --- | --- |
| Benzyl acetate | 500 |
| Hexylcinnamic aldehyde | 1000 |
| ˣ(2E,6Z)-2,6-nonadien-1-ol* | 5 |
| ˣCitronellol | 500 |
| Coumarine | 300 |
| ˣγ-Dodecalactone | 50 |
| Lorysia ®[1] | 1000 |
| Heliotropine | 200 |
| ˣIsobutylquinoleine | 50 |
| ˣLilial ® | 2500 |
| ˣMayol ® | 1000 |
| Phenethylol | 400 |
| ˣPhenylhexanol | 1500 |
| Polysantol ® | 500 |
| Total | 9505 |

*in dipropylene glycol
ˣactive compound according to the present invention
[1] 4-(1,1-dimethylethyl)-1-cyclohexyl acetate; origin: Firmenich SA, Geneva, Switzerland The composition thus prepared showed an anti-microbial activity of 100% against *Escherichia coli, Pseudomonas aeruginosa* and *Staphylococcus aureus*, as measured by the test according to the present invention.

Example 2

A perfuming composition was prepared by using the following ingredients:

| Ingredients | Parts by weight |
| --- | --- |
| Benzyl acetate | 500 |
| Linalyl acetate | 500 |
| ˣCitronellol | 300 |
| ˣCyclamen aldehyde | 100 |
| ˣγ-Dodecalactone | 20 |
| ˣGeraniol | 200 |
| Habanolide ®[1] | 500 |
| ˣLilial ® | 1000 |
| ˣMayol ® | 300 |
| Phenethylol | 800 |
| ˣPhenylhexanol | 500 |
| Benzyl salicylate | 800 |
| Terpineol | 1000 |
| Total | 6520 |

ˣactive compound according to the present invention
[1] mixture of pentadec-11-en-15-olide and pentadec-12-en-15-olide; origin: Firmenich SA, Geneva, Switzerland The composition thus prepared showed an anti-microbial activity of 100% against *Escherichia coli, Pseudomonas aeruginosa* and *Staphylococcus aureus*, as measured by the test according to the present invention.

Example 3

There was prepared a perfuming composition using the following ingredients:

| Ingredients | Parts by weight |
| --- | --- |
| ˣNonanal | 10 |
| Hexylcinnamic aldehyde | 800 |
| ˣIntreleven aldehyde | 10 |
| ˣ4-Undecanolide | 10 |
| ˣCitronellol | 1500 |
| ˣGeraniol | 1000 |
| Habanolide ®[1] | 800 |
| Iralia ® Total[2] | 200 |
| Isopentyrate[3] | 400 |
| Dorisyl[1] | 800 |
| Lyral ®[4] | 500 |
| ˣPhenylhexanol | 1000 |
| ˣTetrahydrolinalool | 1500 |
| Total | 8530 |

ˣactive compound according to the present invention
[1] see Example 2
[2] methylionone mixture; origin: Firmenich SA, Geneva, Switzerland
[3] 1,3-dimethyl-3-butenyl isobutyrate; origin: Firmenich SA, Geneva, Switzerland
[4] mixture of 4- and 3-(4-hydroxy-4-methylpentyl)-3-cyclohexene-1-carbaldehyde; origin: International Flavors & Fragrances, USA The composition thus prepared showed an anti-microbial activity of 100% against *Escherichia coli, Pseudomonas aeruginosa* and *Staphylococcus aureus*, as measured by the test according to the present invention.

Example 4

Activity of anti-microbial perfuming compositions in a fabric softener:

The in vitro Bacterial Contact Time (BCT) test provides a measure of the efficacy with which a product solution, at a certain concentration, will kill a given type of bacteria in the solution. This test is described in the international patent application WO 98/16194, the content of which is here-in-cluded by reference.

General Method:

Three different anti-microbial compositions of the invention containing different percentages of active compounds formulated at 1%, were tested in a fabric softener base prepared from the following ingredients:

| Ingredients | Parts by weight |
| --- | --- |
| Stepantex ® VS90[1)] | 16.5 |
| CaCl$_2$ (10% aqueous solution) | 0.2 |
| Dye (1% aqueous solution) | 0.3 |
| Water | 82.0 |
| Total | 99.0 |

[1)]origin: Stepan, France
The bacteria used in this study were *Escherichia coli* ATCC 10536 (gram-) (origin: American Type Culture Collection, Rockville, Md).

The test organisms were grown in Tryptone Soya Broth (TSB) at 37° C. (OD$_{600}$=1.0). After a 5 times dilution of the initial inoculum (OD$_{600}$=0.2), 100 μl of bacteria were mixed with 100 μl of the sample softener. The bacteria kill was measured by sampling the bacteria/softener mix at short time intervals (respectively 30, 60, 90, 120, 180, 155 and 300 s); and then stopping the kill reaction by a dilution in TSB. When the reaction time was reached, 5 μl of the preparation were diluted into 500 μl and 5 μl of this last preparation were diluted again into 50 volumes TSB. 50 μl of the latter dilution were then plated on a Tryptone Soya Agar (TSA) plate and incubated overnight at 37° C. The average colony number was estimated with a Countermat Flash (IUL Instruments).

Table 1 below reports the time (in s) required to achieved at least 99% kill, for respectively the unperfumed fabric softener base and the same base perfumed at 1% with 3 different antibacterial compositions of the invention, namely:

anti-microbial composition 1 (AC 1) which is the composition described in Example 2 and which contains 37% of active compounds according to the invention;

anti-microbial composition 2 (AC 2) which is the composition described in Example 3 and which contains 59% of active compounds according to the invention; and anti-microbial composition 3 (AC 3) which contains 100% of active compounds according to the invention and which was prepared by using the following ingredients:

| Ingredients | Parts by weight |
| --- | --- |
| Nonanal | 10 |
| Intreleven aldehyde | 10 |
| 4-Undecanolide | 10 |
| Citronellol | 1500 |
| Geraniol | 1000 |
| Phenylhexanol | 1000 |
| Tetrahydrolinalool | 1500 |
| Total | 5030 |

TABLE 1

Bacterial Contact Test carried out respectively on a fabric softener base unperfumed and on the same base perfumed with 3 different compositions

| Composition tested | Percentage of active ingredients | Time for kill [s] 99% |
| --- | --- | --- |
| Softener base (SB) unperfumed | 0 | 300 |
| SB perfumed with AC 1 | 37 | 255 |
| SB perfumed with AC 2 | 59 | 90 |
| SB perfumed with AC 3 | 100 | 30 |

It clearly appears from these results that the softener base comprising the anti-microbial compositions of the invention performed better than the base alone which required at least 300 s to reach a 99% kill. Composition of fabric softener and AC 3 (containing 100% active ingredients) also attained a 99.9% kill after a contact time of 90 s. Probability values for 99 and 99.9% kills were 0.1 and 0.01 respectively.

What is claimed is:

1. A method to prepare a perfuming composition or a perfumed article which has anti-microbial activity against at least 2 different kinds of bacteria selected from the group consisting of *Escherichia coli*, *Pseudomonas aeruginosa*, *Staphylococcus aureus* and *Enterococcus hirae*, which comprises:

(i) testing a perfuming ingredient to determine if it has the desired anti-microbial activity by:

solubilizing the perfuming ingredient in an aqueous medium at a concentration between 250 and 1000 μg/ml, relative to the aqueous medium, in the presence of an effective amount of a testing solvent which is substantially non-toxic for the different types of bacteria that are to be tested and which allows complete solubilization of said perfuming ingredient;

adding an inoculum of the different types of bacteria that are to be tested such that the concentration of the bacteria in the aqueous medium is at least $10^7$ colony forming units/ml;

diluting the aqueous medium so as to reduce the concentration of the bacteria therein to $10^3$ colony forming units/ml;

spreading a volume of a diluted aqueous medium of $10^2$ colony forming units of the bacteria onto a culture medium;

counting the surviving colonies after incubation;

comparing the number of surviving colonies obtained with that of a control that does not contain said perfuming ingredient; and selecting only those perfuming ingredients which have 100% effectiveness against at least 2 different kinds of bacteria to form the anti-microbial perfuming composition or perfumed article; and (ii) preparing the perfuming composition or perfumed article by admixing with other perfuming ingredient(s), solvent(s) and adjuvant(s) of current use in perfumery at least 30% by weight of one or more of the selected perfuming ingredients that have the 100% effectiveness against the at least 2 different kinds of bacteria.

2. The method according to claim 1, wherein the testing solvent is an alcohol.

3. The method according to claim 2, wherein the alcohol is ethanol.

4. The method according to claim 3, wherein the ethanol is present at a concentration in the aqueous medium of between 5 to 20% by weight with respect to the total weight of the aqueous medium.

5. The method according to claim 1, wherein the bacteria that are to be tested contacts the aqueous medium for a time of about 5 min before the dilution of the aqueous medium.

6. The method according to claim 1, wherein the perfuming ingredient is present in the aqueous medium at a concentration of between 400 and 600 µg/ml.

7. The method according to claim 1, wherein the perfuming ingredient(s) represent at least 50% by weight of the perfuming composition.

8. The method according to claim 1, wherein the perfuming ingredient is selected from the group consisting of decanal, 10-undecen-1-al, nonanal, 4-isopropylbenzaldehyde, 4-undecanolide, citronellal, citronellol, cyclamen aldehyde, delphone, dihydroeugenol, 8-p-menthanol, dimetol, geraniol, 3-(1,3-benzodioxal-5-yl)-2-methylpropanal, isoeugenal, nerol, tetrahydrolinalool, zestover, intreleven aldehyde, (2E, 6Z)-2,6-nonadien-1-ol, γ-dodecalactone, floralozone, isobutylquinoleine, butylphenyl methylpropional, cis-7-p-menthanol, phenylhexanol, and 9-decen-1-ol.

9. The method of claim 1 wherein the perfuming composition or article is incorporated in or is present as a soap, a bath or shower gel, a shampoo or other hair-care product, a deodorant or anti-perspirant, a cosmetic preparation, an air-freshener, a liquid or solid detergent for the treatment of textiles, a fabric softener, or an all purpose cleaner for household or industrial use.

* * * * *